US008853283B2

(12) United States Patent
Platscher et al.

(10) Patent No.: US 8,853,283 B2
(45) Date of Patent: Oct. 7, 2014

(54) STABLE CRYSTAL MODIFICATIONS OF DOTAP CHLORIDE

(75) Inventors: Michael Platscher, Schlatt (CH); Alfred Hedinger, Thayngen (CH)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 11/720,263

(22) PCT Filed: Nov. 7, 2005

(86) PCT No.: PCT/EP2005/011874
§ 371 (c)(1),
(2), (4) Date: May 25, 2007

(87) PCT Pub. No.: WO2006/056312
PCT Pub. Date: Jun. 1, 2006

(65) Prior Publication Data
US 2008/0014254 A1    Jan. 17, 2008

(30) Foreign Application Priority Data
Nov. 26, 2004   (DE) .......................... 10 2004 057 303

(51) Int. Cl.
A61K 47/16     (2006.01)
A61K 39/00     (2006.01)
C07C 219/08    (2006.01)

(52) U.S. Cl.
CPC .................................. *C07C 219/08* (2013.01)
USPC ........ 514/788; 514/785; 514/560; 424/184.1; 424/450; 560/171; 560/155

(58) Field of Classification Search
USPC ................ 514/2, 44, 785, 788; 560/171, 155; 424/450, 184, 489, 184.1
See application file for complete search history.

(56) References Cited

U.S. PATENT DOCUMENTS 5,264,618 A * 11/1993 Felgner et al. ................ 560/224
6,846,935 B2    1/2005 Alcon-Marruga et al.

FOREIGN PATENT DOCUMENTS

WO    WO 2005/049549 A    6/2005

OTHER PUBLICATIONS

Perissi, et al., Electron Spin Resonance and Differential Scanning Calorimetry as Combined Tools for the Study of Liposomes in the Presence of Long Chain Nitroxides, Journal of Physical Chemistry B, 2002, 106(40), pp. 10468-10473, (abstract) Chemical Abstract Services, Columbus OH.*
Pfohl, et al., Biological Polyelectrolyte complexes in solution and confined on patterned surfaces, 2002, 198-200, Colliods and Surfaces, A: Physicochemical and Engineering Aspects, pp. 613-623, (abstract) Chemical Abstract Services, Columbus OH.*
Kim, Y. J., et al., Counterion effects on Transfection Activity of Cationic Lipid Emulsions, 2001, Biotechnol. Bioprocess Eng., vol. 6, pp. 279-283.*
Caldwell, J., Do single enantoimers have something special to offer?, 2001, Human Psychopharmacoloty, Hum. Psychopharmacl dlin Exp. 16, pp. S67-S71.*
Grupp, P.W., Patents for Chemicals, Pharmaceuticals and Biotechnology, 1999, Oxford University Press, Chapter 11, pp. 199-200 (6 pages).*

(Continued)

*Primary Examiner* — Yate K Cutliff
(74) *Attorney, Agent, or Firm* — Millen, White, Zelano, Branigan, P.C.

(57) ABSTRACT

The invention relates to enantiomerically pure DOTAP chloride and stable crystal modifications of (2R,S)-, (2S)- and (2R)-DOTAP chloride, to a process for the preparation of these modifications, and to the use thereof as constituent for the preparation of medicaments.

3 Claims, 6 Drawing Sheets (principal phase transition temperatures)

(56) References Cited

OTHER PUBLICATIONS

Mansfield, P., et al., Single-Enantiomer Drugs, Mar. 1, 2004, Clinical Pharmacokinet, vol. 43, issue 5, pp. 287-290.*

Strong, M., FDA Policy and Regulations of Stereoisomers: Paradigm shift and the future of safer, more effective drugs, 1999, Food & Drug L.J., vol. 54, pp. 463-487.*

Alberts, B. et al., Isolating cells and growing them culure, chapter 8, 2002, Molecular Biology of he Cell, 4th edition, (14 pages).*

Perissi, Ilaria et al., Electron Spin Resonance and Differential Scanning Calorimetry as Combined Tools for the Study of Liposomes in the Presence of Long Chain Nitroxides, Journal of Physical Chemistry B, 2002, 10468-10473, 106(40), Chemical Abstract Service, Columbus OH.

Pfohl, T. et al., Biological Polyelectrolyte Complexes in Solution and Confined on Patterned Surfaces, Colloids and Surfaces, A: Physicochemical and Engineering Aspects, 2002, pp. 613-623, Chemical Abstracts Service, Columbus OH.

Barbier Pierre et al., "Allergenic α-Methylene-γ-butyrolactones. Stereospecific Syntheses of (+)- and (−)-γ-Methyl-α-methylene-γ-butyrolactones. A Study of the Specificity of (+) and (−) Enantiomers in Inducing Allergic Contact Dermatitis", J. Med. Chem. 1982, 25, 943-946.

http:/www.liposomes.org/2011/03/what-is-effect-of-phase-transition.html—Encapsula Nano Sciences, Sunday Mar. 13, 2011, "What is the effect of the phase transition temperature of the lipid on the liposome formulation?" Jul. 12, 2011.

Aljaberi et al., "Physiochemical properties affecting lipofection potency of a new series of 1,2-dialkoylamidopropane-based cationic lipids", Colloids Surf B Biointerfaces, May 15, 2007; 57(1): 108-117.

Vasievich, E.A. et al., "Effects of enantiomerically pure vaccine formulations on a murine cervical cancer model", University of North Carolina, Scripps Research Institute, 2010.

Karen Smith Korsholm et al., "Cationic liposomal vaccine adjuvants in animal challenge models: overview and current clinical status", Expert Rev. Vaccines, vol. 11(5), pp. 561-577, (2012).

Elizabeth A. Vasievich et al., "Enantiospecific adjuvant activity of cationic lipid DOTAP in cancer vaccine", Cancer Immunol Immunother, vol. 60, pp. 629-638, (2011).

Roberto Bei et al., "The use of a cationic liposome formulation (DOTAP) mixed with a recombinant tumor-associated antigen to induce immune responses and protective immunity in mice", Journal of Immunotherapy, vol. 21(3), pp. 159-169, (1998).

* cited by examiner

Fig. 4 (type IV)

Fig. 5 (amorphous)

(principal phase transition temperatures)

STABLE CRYSTAL MODIFICATIONS OF DOTAP CHLORIDE

The present invention relates to enantiomerically pure DOTAP chloride and crystal modifications of racemic and enantiomerically pure DOTAP chloride, to a process for the preparation thereof, and to the use thereof for the preparation of pharmaceutical compositions.

DOTAP chloride above and below denotes N,N,N-trimethyl-2,3-bis[[(9Z)-1-oxo-9-octadecenyl]oxy]-1-propanaminium chloride, also known as (Z,Z)—N, N, N-trimethyl-2,3-bis[(1-oxo-9-octadecenyl)oxy]-1-propanaminium chloride or 1,2-dioleoyloxy-3-trimethylammonium propane chloride, and the hydrates thereof.

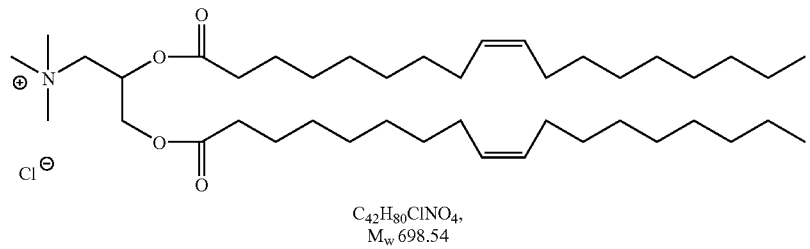 [SMILES: CCCCCCCC/C=C\CCCCCCCC(=O)OCC(C[N+](C)(C)C)OC(=O)CCCCCCC/C=C\CCCCCCCC ; [Cl-]]

$C_{42}H_{80}ClNO_4$, $M_w$ 698.54

CAS numbers: 132172-61-3 and 477274-39-8 (racemate), 197974-73-58 (racemate, monohydrate)
428506-51-8 (2S form), 328250-28-8 (2R form)

Liposomes are synthetic multilayered vesicles (spherically self-contained membranes) comprising ambiphilic substances, usually natural lipids, into which both hydrophilic substances can be encapsulated into the aqueous interior, and also lipophilic substances can be incorporated into the inside of the lipid membrane.

They are employed in particular in cosmetics and in medicine, especially in dermatology. Here, in particular vitamins, coenzymes, skin-care agents and sunscreens are embedded. Liposomes are generally applied topically.

However, liposomes are increasingly achieving further importance in pharmaceutical technology, since parenteral application of liposomes enables more specific organ distribution to be achieved than if the active compounds are used in freely dissolved form.

If DNA, RNA or proteins are incorporated, lipoplexes are obtained.

Addition of oils and the use of high-pressure homogenisers enables the formation of so-called nanoparticles (nanoparts) to be forced from liposomes. These are particles of approximately the same size as liposomes, but which do not have a water phase, but instead an oil phase in their interior. They are particularly suitable for the encapsulation of lipophilic substances.

Microemulsions are colloidally disperse, single-phase systems comprising aqueous, lipid-like and surfactant components. They have a particle size of 1-500 nm and behave in a similar manner to liquids.

Especially in connection with peptidic active compounds, nucleotides, vaccines and other biopharmaceuticals, which normally have poor solubility, the solubilising effect has very great importance in the case of the applications described above.

In addition, degradation of the active compounds in the body can be slowed and a sustained-release effect achieved in this way.

DOTAP chloride belongs to the class of cationic lipids. In contrast to naturally occurring phospholipids, these do not have a zwitterionic character. Liposomes comprising cationic lipids, alone or combined with phospholipids or other lipid-like compounds, have a positively charged surface. This gives rise to high affinity to cells which have a negatively charged surface on the outside, for example endothelial cells.

Particularly important, however, is the ability of DOTAP-based and other cationic liposomes and lipoplexes to penetrate into cells and thus to transport the active compounds incorporated therein into the interior of the cell (transfection).

All these properties make DOTAP chloride very interesting for cancer therapy too. These properties give rise to the possibility of applying conventional cytostatic agents incorporated in cationic DOTAP liposomes.

The transfection properties of DOTAP chloride and other DOTAP salts, such as, for example, the acetate, bromide, dihydrogenphosphate, hydrogensulfate, iodide, mesylate, methylsulfate, trifluoroacetate, sulfate or disulfate and triflate, are adequately known from the literature.

DOTAP dihydrogenphosphate and DOTAP mesylate are only mentioned as racemate in the literature. All other salts mentioned above are each mentioned as racemate and as 2S-enantiomer, and in addition the 2R-enantiomers of the chloride and methylsulfate are mentioned.

In some in-vitro studies, other salts, such as, for example, DOTAP methylsulfate, have achieved better transfection rates than DOTAP chloride.

Used in vivo, however, anion exchange at the liposome surface takes place in the living body, meaning that the advantages of other salts do not arise here. Especially on medical use in humans in particular for parenteral application, DOTAP salts with physiologically acceptable anions, such as, for example, the corresponding chloride or the acetate, are therefore preferred.

Medical, in particular parenteral applications make the highest demands of the quality and purity of the active compounds and adjuvants used. There are therefore very strict regulations on the part of the authorities with respect to the preparation, reproducibility of preparation and by-product profile of these compounds. In the case of substances used parenterally, microbiological contamination by pathogenic microorganisms and endotoxins must, in addition, be strictly avoided and controlled.

DOTAP chloride and other DOTAP salts are extremely unstable and are therefore difficult per se to prepare in an acceptable purity so that they are suitable for use for the preparation of a medicament formulation.

Like all lipids which carry oleic acid radicals, such as, for example, the natural phospholipids DOPC and DOPE, all DOTAP salts are very sensitive to oxidation. However, the oxidation products of unsaturated fatty acid derivatives generally have high toxicity.

Suitable preparation and purification methods are required here. DOTAP acetate, for example, is in the form of a high-boiling oil and industrially can therefore only be obtained with great difficulty in adequate quality.

The conventional methods of overcoming the instability, such as, for example, the addition of antioxidants in the form of ascorbic acid or reduced L-glutathione, greatly restrict the general usability of DOTAP chloride since interactions with the active compounds to be embedded later cannot be excluded. Complete exclusion of oxygen during the preparation, storage and use is virtually impossible or can only be facilitated with very great effort.

DOTAP chloride is commercially available only as a chloroform solution or as an amorphous solid.

In addition to its oxidation sensitivity, amorphous DOTAP chloride is also extremely hygroscopic and deliquesces within an extremely short time at normal atmospheric humidity levels to give a greasy film. This makes handling of this compound much more difficult.

Thus, the manufacturer of amorphous DOTAP chloride generally recommends storage under protective gas at −20° C. and only guarantees a shelf life of about 6 months.

The literature only reveals various synthetic routes for the preparation of amorphous, racemic DOTAP chloride:

Eibel and Unger, DE4013632A1, outline the synthesis of DOTAP chloride from DOTAP bromide by ion exchange in the chloroform/methanol/aqueous HCl solvent system followed by purification by means of chromatography. DOTAP bromide is obtained in advance in situ from 1-bromo-2,3-dioleoyloxypropane.

Leventis and Silvius, Biochim. Biophys. Acta, 1023 (1990) 124-132, report on the synthesis of DOTAP chloride from DOTAP iodide by ion exchange in the two-phase solvent/NaCl solution system. DOTAP iodide is obtained in advance by methylation of the corresponding dimethylamino compound by means of methyl iodide.

Nantz et al., Biochim. Biophys. Acta, 1299 (1996) 281-283, J. Med. Chem. 40 (1997) 4069-4078, describe the synthesis of DOTAP chloride by non-aqueous ion exchanger chromatography. The desired compound is obtained by evaporation of the eluate.

Felgner et al., U.S. Pat. No. 5,264,618, carry out the methylation of the corresponding dimethylamino compound directly to DOTAP chloride by means of methyl chloride. They apparently obtain a yellow wax by crystallisation from acetonitrile at −20° C. However, DOTAP chloride is virtually insoluble in acetonitrile at room temperature. Attempts to reproduce this so-called crystallisation gave only amorphous material through solidification of the oily substance obtained from hot solution on cooling. The fact that this is not a crystallisation is also evident from the fact that the authors apparently do not achieve a purification effect and have to purify the substance by chromatography.

Consequently, neither synthetic routes for the preparation of the two enantiomeric DOTAP chlorides nor characteristic properties thereof are known to date. Although Chemical Abstracts has assigned numbers for the two enantiomers, the corresponding publications describe exclusively work with racemic DOTAP chloride.

In particular if the compounds are intended for parenteral use, a preparation which includes treatment with ion exchanger resin is extremely problematical in view of possible microbiological contamination, since corresponding resins are an ideal nutrient medium for bacteria and even after they have been killed, a risk of contamination by endotoxins still remains.

The object of the present invention is therefore to provide DOTAP chloride salts and hydrates in high purity and with adequate chemical and physical stability. A further object of the present invention is to provide these salts with long shelf lives, enabling them to be used for the preparation of pharmaceutical formulations. There continues to be a great demand for a reproducible process for the preparation of stable forms of DOTAP chloride salts and hydrates which can be carried out on an industrial scale.

Enantiomerically pure DOTAP chloride can be obtained from enantiomerically pure starting materials analogously to the processes described for the racemate, i.e.
via (R or S)-1-chloro-2,3-dioleoyloxypropane,
via (R or S)-1-LG-2,3-dioleoyloxypropane and ion exchange (LG=leaving group) or via (R or S)-1-dimethylamino-2,3-dioleoyloxypropane.

A further preparation method which may be mentioned is racemate resolution of racemic DOTAP chloride.

By means of experiments, it has now been found, surprisingly, that both racemic and also enantiomerically pure, crystalline DOTAP chloride can be obtained in a simple manner with high chemical purity and excellent stability. The crystalline products obtained in this way have virtually unlimited stability at room temperature under protective gas. They are therefore suitable as constituent or as starting material for the preparation of medicament forms.

The present invention accordingly relates to enantiomerically pure DOTAP chloride and stable crystal modifications of racemic and enantiomerically pure DOTAP chloride.

The stable crystal modifications can be in crystalline and partially crystalline form. They have a never hitherto achieved purity of >98% together with a never hitherto achieved stability of >98% in relation to the starting value after storage for 12 months with exclusion of air at 25° C. and 60% relative atmospheric humidity. (see in this respect Table 1). The DOTAP chloride crystal modifications have a content of less than 1 equivalent of water or solvent of crystallisation per equivalent of DOTAP chloride.

The racemic DOTAP chloride crystal modifications exist, for example, in three different crystal modifications (type I, type II, and type III) and exhibit moderately sharp bands in powder X-ray diffraction measurements (see in this respect FIG. 1 to FIG. 3 and Table 2).

Selected 2 theta values for the various crystal modifications are 12.6, 19.5, 20.2, 21.5 and 25.2 (type 1); or 3.3, 4.9, 19.3, 20.0 and 23.5 (type II); or 2.8, 5.8, 20.0, 21.2 and 25.1 (type III).

Enantiomerically pure DOTAP chlorides are likewise obtained in crystalline form. Selected 2 theta values for the crystal modification found are 12.8, 19.4, 19.8, 20.2, and 21.5 (type IV, see in this respect FIG. 4).

The enantiomers are optically active. Thus, (2S)-DOTAP chloride has an optical rotation of −2.12°, (2R)-DOTAP chloride has an optical rotation of +2.12° ($[\alpha]_D$ at 20° C., 1% solution in dichloromethane).

The invention furthermore relates to a process for the preparation of DOTAP chloride crystal modifications which is characterised in that DOTAP chloride is crystallised from an aprotic medium. The aprotic medium used for this purpose can be aprotic solvents or mixtures thereof.

The aprotic medium may also comprise protic solvents, such as, for example, water, in small amounts. In exceptional cases, 25% by weight of protic solvents may also be present under suitable conditions. The crystallisation of the DOTAP chlorides can be carried out here directly from the reaction solution without prior purification. Likewise, crystalline DOTAP chloride can be obtained by recrystallisation of amorphous, partially crystalline or crystalline material.

Suitable aprotic solvents are, in particular,
ethers, such as, for example, tetrahydrofuran, methyltetrahydrofuran, dioxane, diethyl ether, dipropyl ether, diisopropyl ether and methyl tert-butyl ether,
ketones, such as, for example, acetone and 2-butanone, methyl isobutyl ketone, methyl isopropyl ketone,
nitriles, such as, for example, acetonitrile, and
esters, such as, for example, ethyl formate, methyl acetate, ethyl acetate, propyl acetate, isopropyl acetate, butyl acetate, isobutyl acetate, dimethyl carbonate, diethyl carbonate and 1,3-di-oxolidin-2-one.

These solvents may in each case be used in pure form or in the form of a mixture, i.e. it is possible both to use the various aprotic solvents in a group in the form of a mixture and also to employ aprotic solvent types inn the form of a mixture with one another. As already indicated above, protic solvent additions may be present in the aprotic solvent or solvent mixture used.

Protic solvent additions of this type can typically consist of the following solvents:
alcohols, such as, for example, methanol, ethanol, n-propanol, isopropanol, n-butanol, isobutanol, 2-butanol, tert-butanol, 3-methyl-1-butanol and ethylene glycol, methoxyethanol, ethoxyethanol, or
water.

The protic solvent additions may in turn be additions of the pure solvents or of mixtures of these protic solvents.

The crystallisation of the DOTAP chloride modifications is generally achieved specifically by slow cooling of the prepared solution to temperatures below 30° C. The formation of the crystals is carried out either spontaneously or by inoculation with the corresponding DOTAP chloride crystal modification.

The various DOTAP chloride crystal modifications can be converted into one another. The conversions can be achieved by heat treatments of the isolated crystal modifications at elevated temperature or by extended stirring of their suspensions under crystallisation conditions.

The use of amorphous or partially crystalline DOTAP chloride as starting material for the recrystallisation gives, by the process described, essentially crystalline DOTAP chlorides of never hitherto achieved purity together with never hitherto achieved stability.

The invention also relates to the use of crystalline DOTAP chlorides for the preparation of medicament formulations since the crystalline DOTAP chlorides have excellent stability in solid form under the stated conditions and have constant and very good quality for a virtually unlimited time.

In addition, enantiomerically pure DOTAP chlorides have different physical properties to the racemate, in particular in combination with chiral compounds, such as the phospholipids or cholesterol.

The novel properties found for the enantiomerically pure DOTAP chlorides can advantageously be utilised, alone or in combination with suitable phospholipids, cholesterol and derivatives thereof, to provide novel liposome grades which, compared with conventional forms, on the one hand represent closer packings of the lipids and on the other hand have a more uniform structure. Thus, liposomes prepared from the pure enantiomers exhibit a 5° C. higher principal phase transition temperature compared with the liposomes comprising racemic DOTAP chloride. This is a measure of the packing density. Liposomes comprising DOTAP chloride enantiomers therefore also have reduced leaking of the compound incorporated in them.

This has the consequence that liposomes charged with pharmaceutically active compounds will release active compounds in a delayed manner in interaction with the metabolism in the human or animal body. In particular, sensitive active compounds can thus advantageously be transported in a more specific manner to the desired site or organ where the medicament action is desired.

The DOTAP chloride enantiomers also exhibit, in particular in combination with chiral lipids, such as phospholipids, cholesterol and derivatives thereof, transfection properties which differ cell-line-specifically.

For the preparation of these novel liposomes, it is possible for the person skilled in the art specifically to select a form or a certain mixing ratio of the DOTAP chlorides thus provided in order to prepare liposomes having certain novel properties.

The invention consequently furthermore also relates to the pharmaceutical compositions resulting from the use of the DOTAP chloride forms claimed. Pharmaceutical compositions of this type can comprise the crystal modifications of (2R,S)-, (2S)- and (2R)-DOTAP chloride together with other pharmaceutical active compounds and known adjuvants usually employed in medicament preparation, as well as one or more solvents.

These pharmaceutical compositions can, for example, be in the form of liposomes, lipoplexes, microemulsions and nanoparticles and include, for example, an active compound from the group of the peptides, nucleotides, vaccines or cytostatic agents.

The present description enables the person skilled in the art to apply the invention in a comprehensive manner. In addition, the following examples serve for better understanding and for illustration of possible variants of the invention. These examples should therefore in no way be regarded as restrictive.

All temperatures mentioned in the following examples are indicated in degrees Celsius. Unless stated otherwise, content data are given as % by weight.

X-RAY SCANNING INFORMATION REGARDING THE FIGURES

Figure 1:
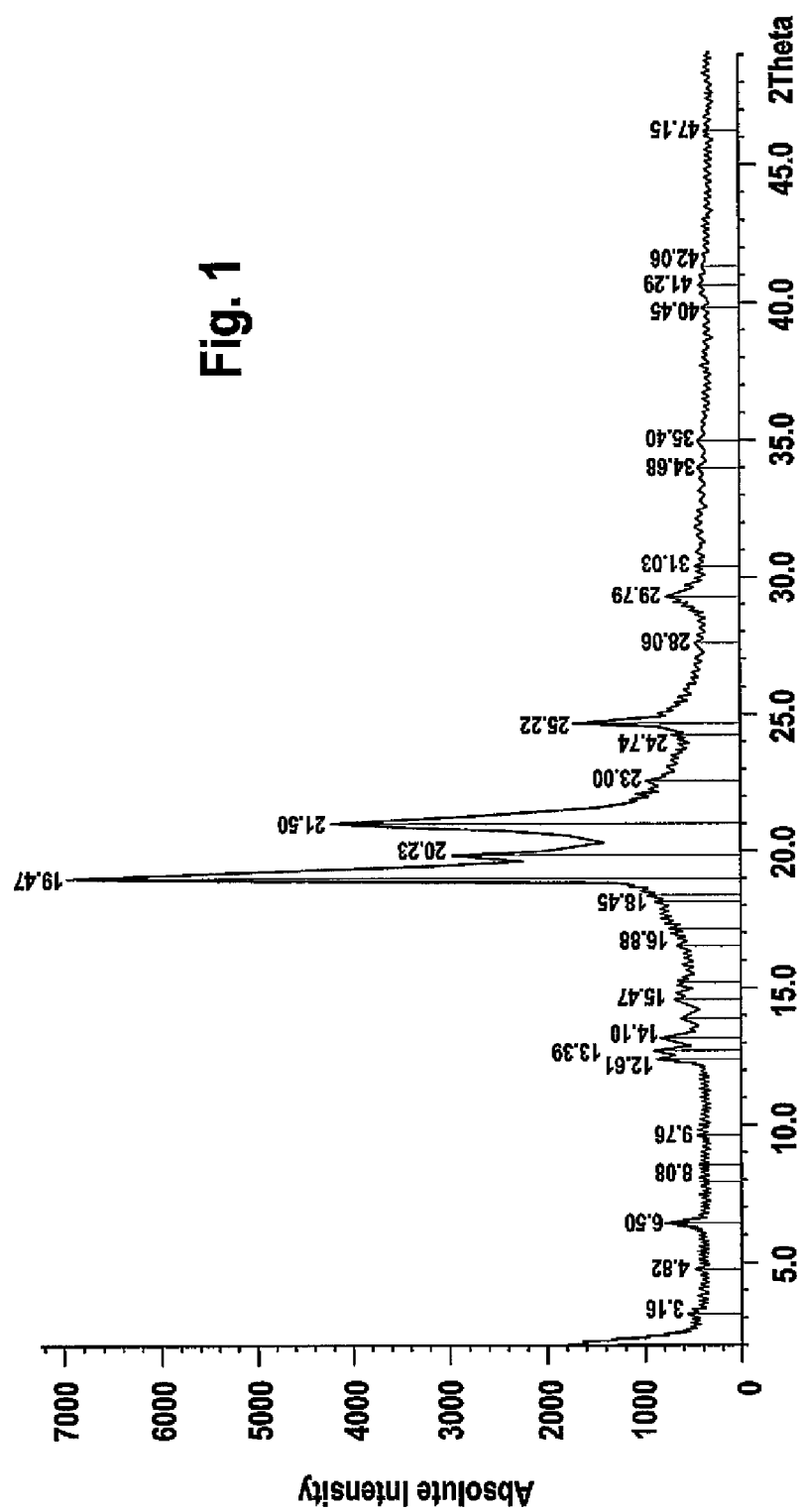
FIG. 1 illustrates x-ray spectra for DOTAP chloride crystalline Type I.

FIG. 1
Comment: Single Measurement-Hygroscopic
Diffract.: Transmission
Monochrome: Curved Germanium (111)
Radiation: 1.54060 Cu
Generator: 55 kV, 30 mA
Detector: Linear PSD/Moving/Fixed Omega
Scan Mode: Transmission
Range 1: 2Theta (begin, end, step)=2.000, 49.980, 0.020
130.0 sec/step Imax=7060 (PSD Step 0.50 10.0 sec/step)

Figure 2:
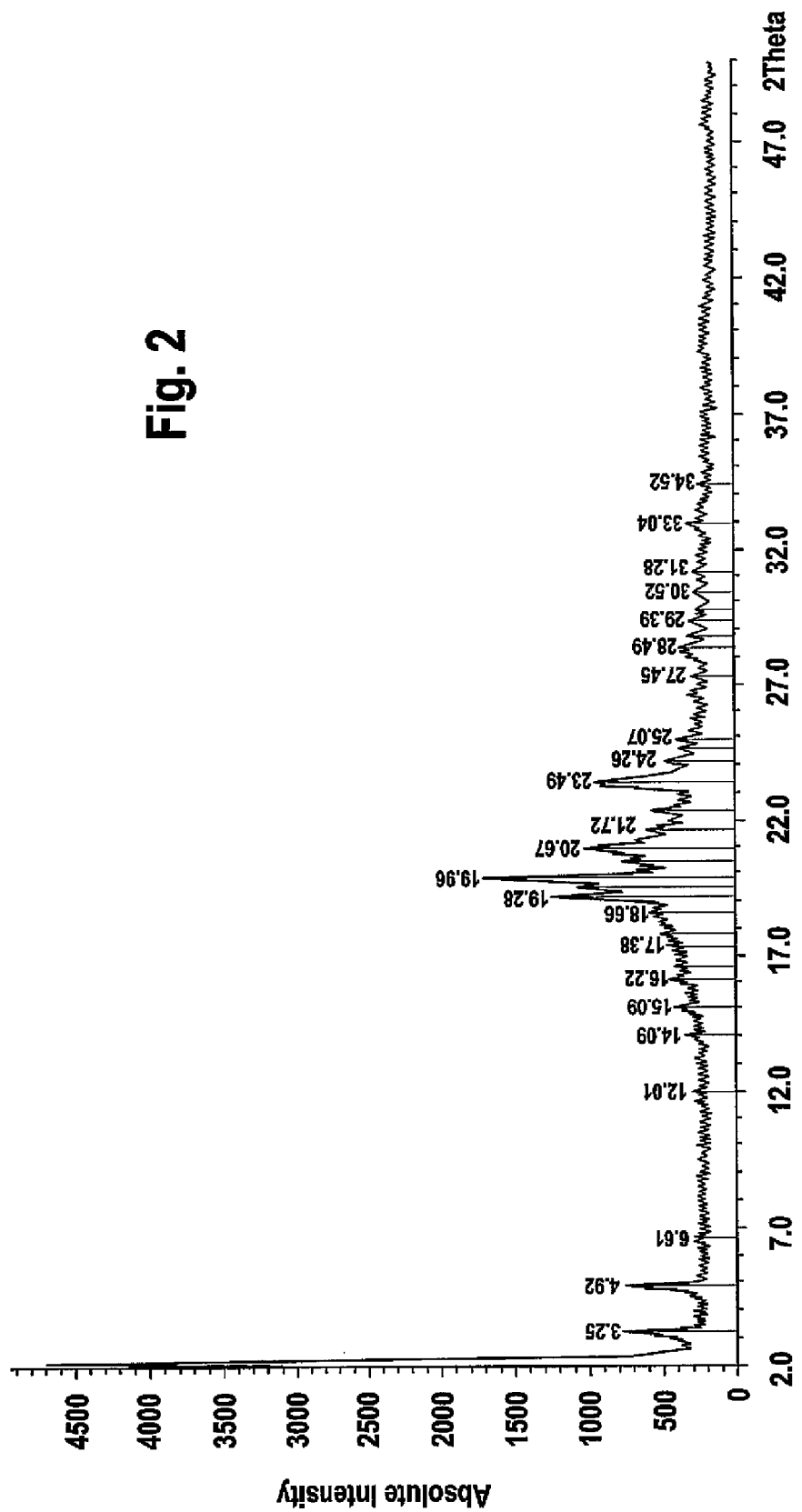
FIG. 2 illustrates x-ray spectra for DOTAP chloride crystalline Type II.

FIG. 2
Diffract.: Transmission
Monochrome: Curved Germanium (111)
Radiation: 1.54060 Cu
Generator: 55 kV, 30 mA
Detector: Linear PSD/Moving/Fixed Omega
Scan Mode: Transmission
Range 1: 2Theta (begin, end, step)=2.000, 49.980, 0.020
130.0 sec/step Imax=4708 (PSD Step 0.50 10.0 sec/step)
FIG. 3
Comment: Single Measurement
Diffract.: Transmission
Monochrome: Curved Germanium (111)
Radiation: 1.54060 Cu
Generator: 55 kV, 30 mA
Detector: Linear PSD/Moving/Fixed Omega
Scan Mode: Transmission
Range 1: 2Theta (begin, end, step)=2.000, 49.980, 0.020
130.0 sec/step Imax=1871 (PSD Step 0.50 10.0 sec/step)
FIG. 4
Diffract.: Transmission
Monochrome: Curved Germanium (111)
Radiation: 1.54060 Cu
Generator: 55 kV, 30 mA
Detector: Linear PSD/Moving/Fixed Omega
Scan Mode Debye-Scherrer
Range 1: 2Theta (begin, end, step)=2.000, 49.980, 0.020
130.0 sec/step Imax=2995 (PSD Step 0.50 10.0 sec/step)
FIG. 5
Diffract.: Transmission
Monochrome: Curved Germanium (111)
Radiation: 1.54060 Cu
Generator: 55 kV, 30 mA
Detector: Linear PSD/Moving/Fixed Omega
Scan Mode Debye-Scherrer
Range 1: 2Theta (begin, end, step)=2.000, 49.980, 0.020
120.0 sec/step Imax=2102 (PSD Step 0.50 10.0 sec/step)

EXAMPLES FOR ILLUSTRATING THE INVENTION

Example 1

Stabilities

In order to determine the stability of crystalline DOTAP chlorides, the substances are stored together with comparative samples at 25° C. and 60% relative humidity with exclusion of air. The remaining content of DOTAP chloride is measured at periodic intervals and quoted in comparison to the initial value.

The purity and content of DOTAP chloride are determined by means of HPLC. For type I, the following values are found:

The stability determination can be repeated at any desired time, the values indicated in Table 1 are reproducible.

TABLE 1

| (R,S)-DOTAP chloride crystalline | Exposure time in months | | | | | |
|---|---|---|---|---|---|---|
| type I | 0 | 1 | 2 | 3 | 6 | 12 |
| Area-% | 100% | 100.0% | 100.0% | 100.0% | 100.0% | 100.0% |
| % by weight | 98.6% | 97.% | 97.9% | 97.2% | 98.2% | 98.7% |

Example 2

Powder X-ray Diagrams

For characterisation of the structural properties (crystal modifications) of crystalline DOTAP chlorides, powder X-ray diagrams (diffraction spectra) of these substances are recorded.

Crystalline DOTAP chlorides give spectra with moderately sharp bands which have relatively good resolution for lipids. The spectra indicate high crystalline contents. No amorphous fractions are visible under the polarising microscope.

Figure 3:
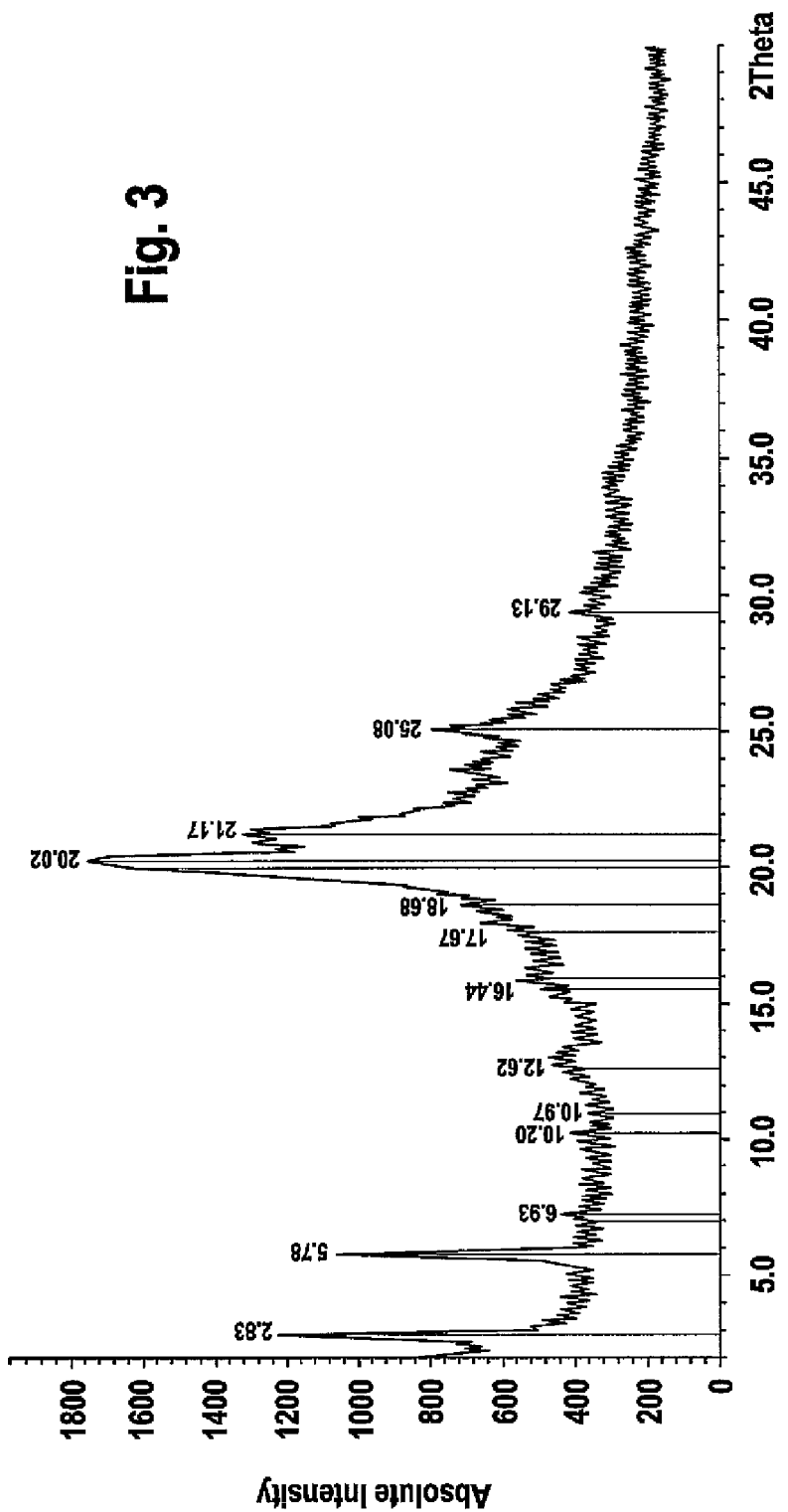
FIG. 3 illustrates x-ray spectra for DOTAP chloride crystalline Type III.
Figure 4:
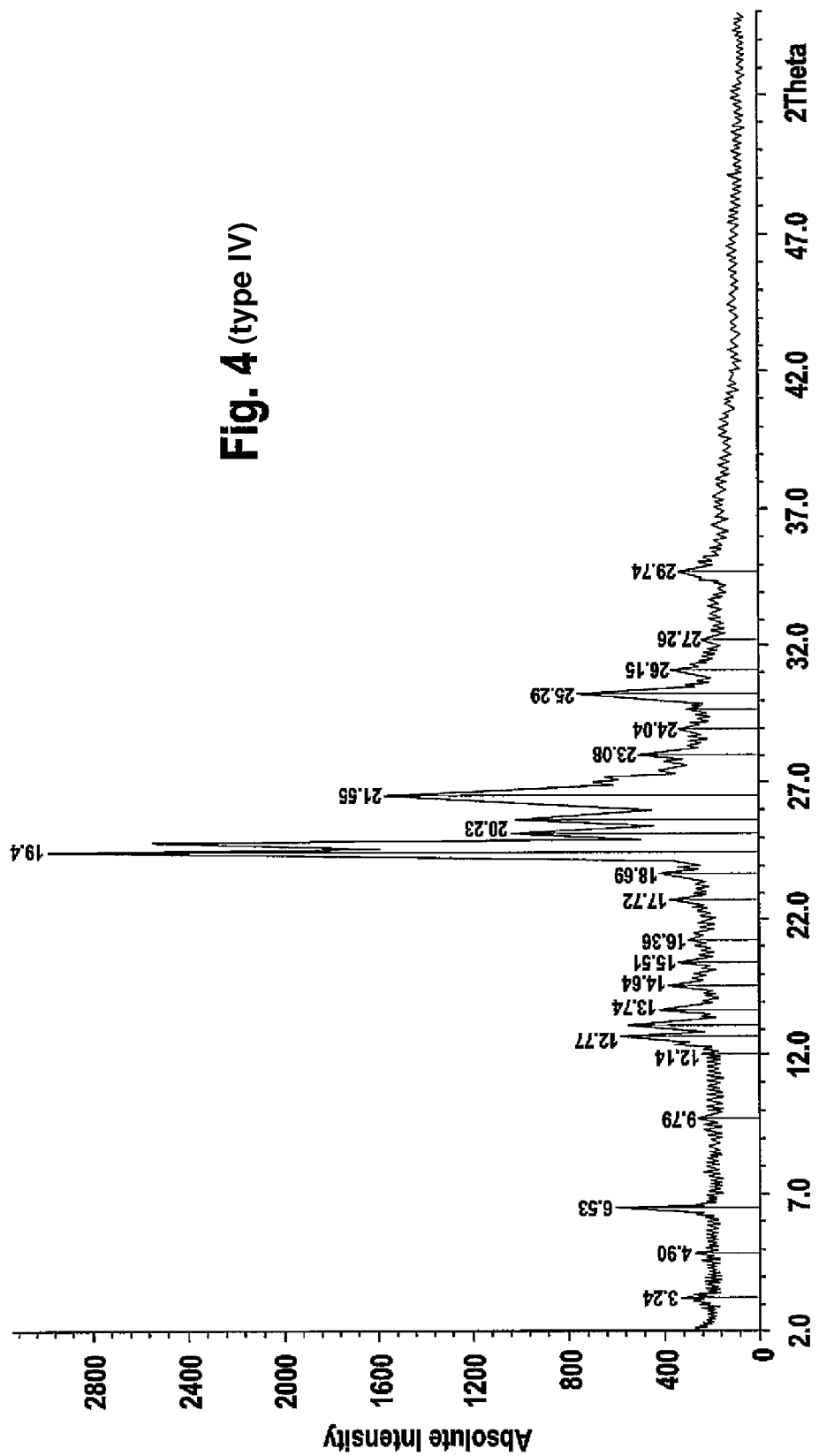
FIG. 4 illustrates x-ray spectra for DOTAP chloride crystalline Type IV.

Examples of spectra are shown in FIG. 1 (type I), FIG. 2 (type II), FIG. 3 (type III) and FIG. 4 (type IV).

Figure 5:
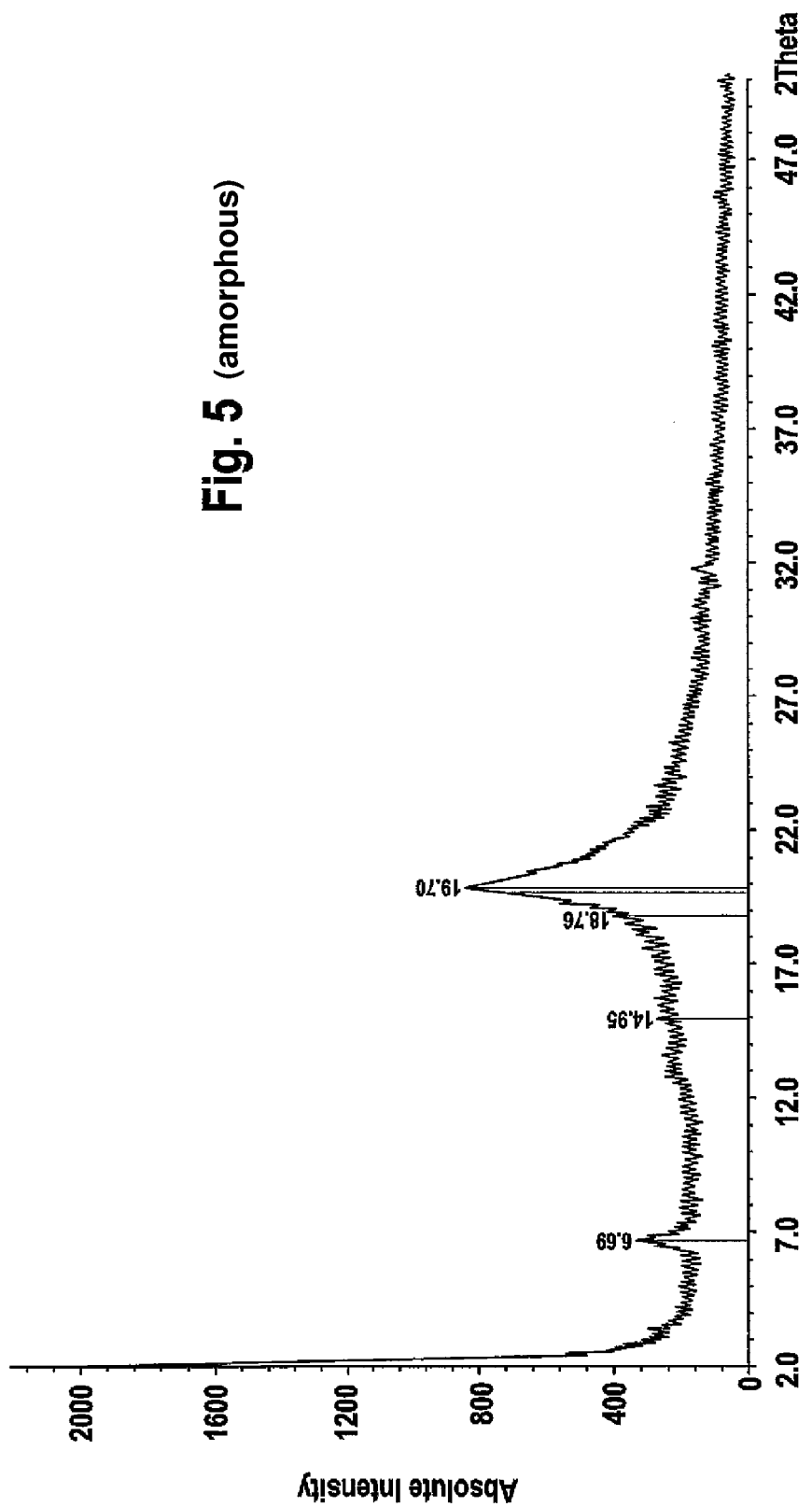
FIG. 5 illustrates x-ray spectra for amorphous DOTAP chloride.

For comparison, a spectrum of a commercially available, amorphous sample is shown in FIG. 5 (amorphous).

Table 2 lists selected 2 theta values for the various crystal modifications of racemic and enantiomerically pure DOTAP chlorides:

TABLE 2

| Type | | Selected 2 theta values |
|---|---|---|
| Type I | racemic | 12.6, 19.5, 20.2, 21.5 and 25.2 |
| Type II | | 3.3, 4.9, 19.3, 20.0 and 23.5 |
| Type III | | 2.8, 5.8, 20.0, 21.2 and 25.1 |
| Type IV | enantiomerically pure | 12.8, 19.4, 19.8, 20.2, and 21.5 |

Example 3

Principal Phase Transition Temperatures

Differential scanning caliometry (DSC) measurements are carried out on multilamellar liposomes in water. Liposomes are prepared by the thin-film method from the calculated amounts of racemic or enantiomerically pure DOTAP chloride. The lipid concentration here is in each case 0.1 g/ml. Suitable amounts of these dispersions are then introduced into sealable aluminium crucibles and measured using a 204 Phoenix calorimeter (Netzsch, Selb, Germany). In each case, three successive heating/cooling runs from −50° C. to +20° C. are carried out at 1° C./min.

Figure 6:
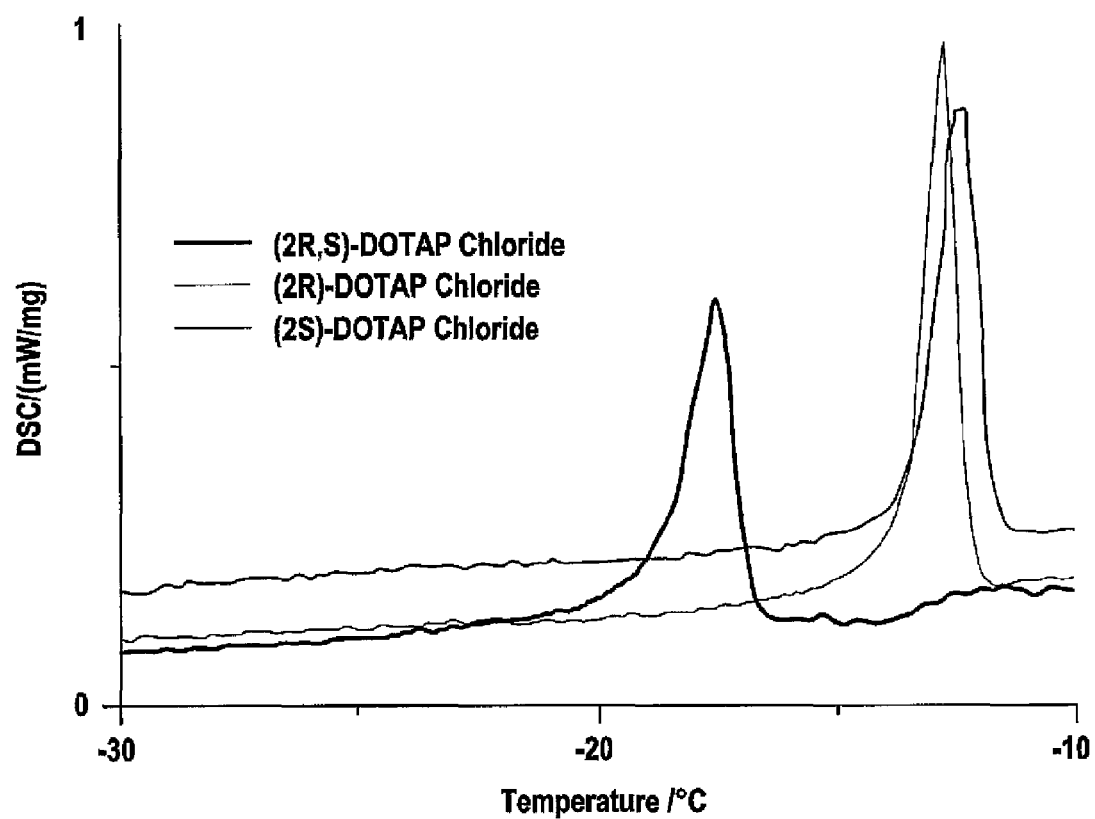
FIG. 6 illustrates DSC curves for (2RS)-, (2R)- and (2S)-DOTAP chlorides.

For all three DOTAP chloride variants, phase transition temperatures below 0° C. are found. For the cooling cycles, this is in each case at −23° C. to −24° C. Differences between racemic and enantiomerically pure DOTAP chloride are in each case evident in the heating cycles. (2R)-DOTAP chloride and (2S)-DOTAP both exhibit an endothermic phase transition around −12.5° C., while the phase transition for the racemate is at −17.5° C. (see FIG. 6).

Example 4

Transfection Properties on COS-7 Cells

Racemic and enantiomerically pure DOTAP chloride and racemic DOTAP methylsulfate are each dispersed with the same amount of cholesterol in the transfection medium and treated with ultrasound. The liposomes and GFP plasmid solution are mixed and incubated for 15 minutes, amounts per 6 well: 2 μg of plasmid/8 μg of lipid.

After incubation for 5 hrs, the supernatant is removed from the cells by suction at 37° C./5% CO2, 2 ml of fresh medium is added, and the mixture is incubated for a further 20 hours. After work-up, FACS analysis shows efficient transfection for all lipoplexes. A significant difference between the transfection rates for the individual lipid mixtures is evident:

| (R)-DOTAP chloride/cholesterol complex: | 32.4% |
|---|---|
| (S)-DOTAP chloride/cholesterol complex: | 11.0% |
| (R,S)-DOTAP chloride/cholesterol complex: | 25.9% |
| (R,S)-DOTAP methylsulfate/cholesterol complex: | 20.2% |

The invention claimed is:

1. A pharmaceutical composition comprising enantiomerically pure (2R)-DOTAP chloride and a pharmaceutically acceptable carrier, with the proviso that the composition is substantially free of (2S)-DOTAP chloride.

2. A pharmaceutical composition according to claim 1, further comprising one or more peptides, nucleotides, vaccines or cytostatic agents, or a mixture thereof.

3. A pharmaceutical composition according to claim 1, further comprising one or more liposomes, lipoplexes, nanoparticles or microemulsions, or a mixture thereof.

* * * * *